United States Patent [19]

Cotter et al.

[11] Patent Number: 4,920,098

[45] Date of Patent: Apr. 24, 1990

[54] NUTRITIONAL SUPPORT OR THERAPY FOR INDIVIDUALS AT RISK OR UNDER TREATMENT FOR ATHEROSCLEROTIC VASCULAR, CARDIOVASCULAR, AND/OR THROMBOTIC DISEASES

[75] Inventors: Richard Cotter, Libertyville; Robert C. Johnson, Westchester; Michael Ward, McHenry; David C. Madsen, Libertyville; Anthony J. Valicenti, Deerfield; Michael P. Menard, Grayslake; Hugh N. Tucker, Barrington, all of Ill.

[73] Assignee: Baxter International Inc., Deerfield, Ill.

[21] Appl. No.: 403,849

[22] Filed: Aug. 28, 1989

Related U.S. Application Data

[63] Continuation of Ser. No. 908,447, Sep. 17, 1986, abandoned.

[51] Int. Cl.$^5$ .................. A61K 37/02; A61K 31/195; A61K 31/715
[52] U.S. Cl. .......................................... 514/2; 514/23; 514/558; 514/560; 514/561; 514/562; 514/564; 514/824; 514/943
[58] Field of Search ............... 514/560, 561, 558, 562, 514/564, 824, 943, 2, 23; 424/95

[56] References Cited

U.S. PATENT DOCUMENTS

| | | |
|---|---|---|
| 3,830,931 | 8/1974 | DeFelice . |
| 3,968,241 | 7/1976 | DeFelice . |
| 4,423,072 | 12/1983 | Stahly . |
| 4,434,160 | 2/1984 | Jeretin et al. ........................ 514/556 |
| 4,438,144 | 3/1984 | Blackburn . |
| 4,513,008 | 4/1985 | Revici et al. . |
| 4,526,902 | 7/1985 | Rubin ................................. 514/560 |
| 4,528,197 | 7/1985 | Blackburn . |
| 4,604,286 | 8/1986 | Kawajiri . |
| 4,678,807 | 7/1987 | Cotter et al. . |
| 4,678,808 | 7/1987 | Ward et al. . |
| 4,687,782 | 8/1987 | Brantman ......................... 514/561 |
| 4,703,062 | 10/1987 | Blackburn et al. . |

FOREIGN PATENT DOCUMENTS

| | | |
|---|---|---|
| 0071995 | 2/1983 | European Pat. Off. . |
| 59-78118 | 10/1982 | Japan . |
| 78118 | 5/1984 | Japan ................................. 514/560 |

OTHER PUBLICATIONS

Trissel, Handbook on Injectable Drugs, 2nd Ed., 1980, "Fat Emulsion, 10% Intravenous", pp. 218-221.

Medium-Chain Triglycerides: An Update, A. C. Bach, ScD, and V. K. Babayan, PhD, Amer. J. of Clin. Nutr. 36, Nov. 1982, pp. 950-962.

Fat Emulsions Containing Medium-Chain Triglycerides in Parenteral Nutrition of Intensive Care Patients, J. Eckert et al., 1980.

Comparison of Glucose, LCT, and LCT plus MCT as Calorie Sources for Parenterally Nourished Rats, Chemical Abstracts, vol. 100, 1982.

Medium-Chain Triglycerides and Parenteral Nutrition, Chemical Abstracts, Animal Nutrition, vol. 95, 1981.

Fat Emulsion 10%, Intravenous, Handbook of Injectable Drugs, Second Edition, L. A. Trissel, American Society of Hospital Pharmacists, 1980, pp. 218-221.

Nutritional Management of the Critically Ill Infant with Complex Congenital Disease, C. P. Greecher, MS, RD et al., Nutrition in Clinical Practice, pp. 97-99, 1986.

Nutrition in Congestive Heart Failure, S. M. Poindexter, R.D. et al., Nutrition in Clinical Practice, pp. 83-88, 1986.

Nutrition and the Heart, S. B. Heynsfield, M.D., Nutrition in Clinical Practice, pp. 81-82, 1986.

*Primary Examiner*—Jacqueline Stone
*Attorney, Agent, or Firm*—Paul C. Flattery

[57] ABSTRACT

A method is provided for individuals under treatment for or at risk of atherosclerotic, vascular, cardiovascular, and/or thrombotic disease by administering a composition which comprises a protein source; a carbohydrate source; and at least one lipid selected from the group consisting of: gamma-linolenic acid; eicosapentaenoic acid; docosahexaenoic acid; sterodonic acid; and linolenic acid. Both an enteral and parenteral composition are provided.

14 Claims, No Drawings

NUTRITIONAL SUPPORT OR THERAPY FOR INDIVIDUALS AT RISK OR UNDER TREATMENT FOR ATHEROSCLEROTIC VASCULAR, CARDIOVASCULAR, AND/OR THROMBOTIC DISEASES

This application is a continuation of application Ser. No. 908,447, filed Sept. 17, 1986 now abandoned.

BACKGROUND OF THE INVENTION

The present invention relates to nutritional formulations for the support and therapy of individuals. More specifically, the present invention relates to nutritional compositions for supporting and/or providing therapy to individuals at risk and/or under treatment for atherosclerotic, vascular, cardiovascular, or thrombotic diseases.

For some time investigators and scientists have noted a relationship between diet and the heart function and related systems. There has always been an appreciation for the cardiovascular effects of obesity and the recognition of widespread prevalence of under nutrition in hospitalized patients with cardiovascular derangements. Accordingly, there have been many attempts to formulate nutritional support for patients at risk for or exhibiting atherosclerotic, vascular, cardiovascular, and/or thrombotic diseases. Poindexter, et al, *Nutrition in Congestive Heart Failure*, Nutrition In Clinical Practice (1986) recognize that specific nutritional deficiencies may cause, precipitate, or aggravate acute heart failure. As Poindexter, et al, point out, nutritional deficiencies have been significant factors in the etiology of heart failure in the Orient and developing countries. It is further noted that nutritional therapy for malnourished cardiac patients in recent years has been considered essential supportive therapy.

Patients suffering from long term congestive heart failure have been found to suffer from cardiac cachexia. Other effects of protein-calorie malnutrition on the heart include hypertension, reduced heart rate, reduction in basal metabolic rate and oxygen consumption, atrophy of the heart muscle mass, electrocardiogram (ECG) abnormalities, and heart failure. Furthermore, when congestive heart failure occurs secondary to valvular heart disease that is treated surgically, nutritional status has a notable effect on the surgical outcome. Performing cardiac surgical procedures on patients in a state of nutritional depletion can result in increased morbidity and mortality, compared to adequately nourished patients.

Typically, patients suffering from congestive heart failure are underweight with poor nutritional status. Patients with congestive heart failure and cardiac cachexia frequently exhibit anorexia and early satiety. Poindexter, et al, state that this is attributed to the natural compensatory mechanism that decreases work of the failing heart. Furthermore, due to hepatic congestion that increases pressure in the abdominal cavity, there is a constant feeling of fullness. Moreover, altered taste sensations and intolerances to food odors limit the patient's desire to eat. Accordingly, liquid nutritional supplements high in nutrient density are desirable. However, as Poindexter notes, this must be tempered with concern about the complications caused by overzealous refeeding of malnourished cardiac patient.

Not only are patients with congestive heart failure and other vascular diseases typically underweight with poor nutritional status, but their energy requirements are greatly in excess of a normal individual's energy requirements. Poindexter, et al, note that energy requirements of a patient with congestive heart failure may be 30-50 percent in excess of basal energy expenditure because of increased cardiac and pulmonary energy expenditure. Indeed, cachectic patients require additional calories for repletion and post-operative cardiac patients require still further increases in caloric intake to meet energy demands. For example, the protein requirement for a normal healthy individual to maintain zero nitrogen balance is 0.5-1.0 g/Kg. The patient with congestive heart failure or the postoperative cardiac patient in contrast can require as much as 1.5-2.0 g/Kg to maintain nitrogen balance.

Not only is nutrition important in treating the patient with atherosclerotic, vascular, cardiovascular, and/or thrombotic disease but it is also important in supporting patients at risk of acquiring these diseases Diet can impact the onset of these diseases in certain individuals.

Accordingly, there is a need for a nutritional composition for supporting and therapeutically treating individuals under treatment for vascular, cardiovascular, or thrombotic diseases. Moreover, there is a need for a nutritional composition for supporting individuals who are at high risk of atherosclerotic, vascular, cardiovascular, and/or thrombotic disease.

SUMMARY OF THE INVENTION

The present invention provides a nutritional composition for supporting and/or providing therapy to individuals at risk or under treatment for vascular, cardiovascular, or thrombotic diseases. The formulation can be administered either as an enternal product or parenterally.

As an enteral product, the formulation comprises a protein source, a carbohydrate source, a fat source, and electrolytes. The protein source preferably includes a high biological value protein, an amino acid solution, branched-chain amino acids, and carnitine. The amino acid solution is designed to provide the essential, conditionally essential, and nonessential amino-acids necessary for efficacious protein metabolism in the face of cardiovascular or thrombotic disease states. The nutritional composition also contains a carbohydrate source. The carbohydrate source preferably includes xylitol and a glucose base carbohydrate.

The lipid component of the nutritional composition comprises long chain triglycerides and medium chain fatty acids. The long chain triglycerides encompass trigylcerides containing fatty acids of 11 to 26 carbons in length. The medium chain fatty acids preferable in the present invention are those that are 6 to 10 carbons in length.

Preferably, the long chain triglycerides comprise marine oils and/or gamma-linolenic acid (GLA) and sterodonic acid. Preferably, the marine oils include linolenic acid and large amounts of two other members of the omega three family: eicosapentaenoic acid (EPA) and docosahexaenoic acid (DHA). These fatty acids are incorporated into cell membranes and serum and give rise to metabolites of the omega-three metabolic pathways. Preferably the long chain triglycerides comprise from approximately 50% to about 25% of the lipid component and the medium chain fatty acids comprises from approximately 75% to about 50% of the lipid component. If GLA is utilized with marine oil preferably approximately three times as much marine oil is used as GLA.

Preferably the protein source comprises approximately 15 to about 25% of the caloric source of the enteral nutritional composition. Most preferably the protein source comprises approximately 20% of the caloric source of the enteral nutritional composition. Preferably, the carbohydrate source comprises approximately 40% to about 75% of the caloric source of the enteral nutritional composition. Most preferably, the carbohydrate source comprises approximately 50% of the caloric source of the enteral nutritional composition. Preferably the lipid component comprises approximately 10% to about 40% of the caloric source of the enteral nutritional composition. Most preferably the lipid component comprises approximately 30% of the caloric source of the enteral nutritional composition.

The parenteral regimen for the composition for providing nutritional support or therapy for individuals at risk or under therapy for atherosclerotic, vascular, cardiovascular, and/or thrombotic disease is preferably modular. However, the parenteral regimen can be delivered modularly or premixed. As a modular regimen the parenteral product includes an injectable solution of: a lipid emulsion; a carbohydrate; carnitine; branched-chain amino acids; and amino acids.

Preferably, the lipid emulsion for injection includes approximately 5 to about 20% of a triacylglycerol oil containing approximately 5 to about 80% eicosapentaenoic acid (EPA) and/or approximately 5 to about 80% gamma-linolenic acid (GLA) and approximately 3 to about 25% sterodonic acid (6, 9, 12, 15-octadecateraenoic acid), with approximately 0.4 to about 1.6% egg or soy bean phospholipid and approximately 2.25% of glycerol or other physiologically acceptable tonicity agent, adjusted to physiological pH with sodium hydroxide. The remaining component(s) of the lipid emulsion is either water or water with medium chain triglycerides.

DETAILED DESCRIPTION OF THE PRESENTLY PREFERRED EMBODIMENTS

The present invention provides a nutritional composition that affords a rational, scientific diet or supplement for individuals at high risk or under treatment for atherosclerotic, tvascular, cardiovascular, and/or thrombotic diseases. The formulation is designed to slow the progression of these diseases, and prevent the onset of acute episodes that can result in the death of such patients. To this end, the present invention provides a composition that includes nutritional substrates that have been shown to effect various biochemical and physiological parameters of vascular, cardiovascular and blood systems. The formulation can be administered either as an enteral product or parenterally.

As an enteral product, the formulation comprises a protein source, a carbohydrate source, a fat source, and preferably electrolytes. The protein source preferably includes a high biological value protein, an amino acid solution, branched-chain amino acids, and carnitine. The high biological value protein comprises the base component. Although any high biological value protein can be utilized preferably the high biological value protein is laotalbumin or soy protein. Whole protein or hydrolysates can be utilized.

The amino acid solution is designed to provide the essential, conditionally essential, and non-essential amino acids necessary for efficacious protein metabolism in the face of cardiovascular or thrombotic disease states. The amino acid solution preferably includes: L-Arginine; L-Leucine; L-Isoleucine; L-Lysine; L-Valine; L-Phenylalanine; L-Histidine; L-Threonine; L-Methionine; L-Tryptophan; L-Alanine; L-Proline; L-Serine; L-Tyrosine; and amino acetic acid. An example of an amino acid solution formulation that will function satisfactorily is TRAVASOL® marketed by Travenol Laboratories, Deerfield, Ill. Of course, depending upon requirements not all of the amino acids must be included in the solution. Of course, other nutrients such as, for example, biologically available sources of taurine and cysteine can be added. Preferably the arginine:lysine ratio is between approximately about 0.7:1 to 1.25:1. Most preferably the ratio is approximately 1:1. Clinical and experimental evidence has shown that an arginine:lysine ratio of 1 to 1 is associated with lower plasma cholesterol levels.

The amino acid and base protein, i.e., high biological value protein, is combined with branched-chain amino acids to achieve a final concentration of approximately 45 to 55 percent branched-chain amino acids (w/w). Most preferably the final concentration of branched-chain amino acids is 50 percent of total protein and amino acid content. The branched-chain amino acid mixture that function satisfactorily is that capable of maintaining essential intake of all three branched-chain amino acids to meet nutritional requirements. The branched-chain amino acids Isoleucine, Leucine, and Valine are preferably included in a 1:1:1 molar ratio. An example of such a branched-chain amino acid formula is BRANCHAMIN® marketed by Travenol Laboratories, Deerfield, Ill. Observations on rats and dogs demonstrate that these cardiac muscles depend more on branched-chain amino acids than on all other amino acids. As previously stated, other amino acids can be utilized; for example, in neonates and infants it may be desirable to include taurine.

Preferably glycine should be supplemented to the protein source, if necessary, to obtain levels typically found in soy protein. It has been found that higher levels of plasma glycine are associated with lowered levels of plasma cholesterol.

The protein source also preferably includes L-carnitine. The L-carnitine is added to achieve a final concentration of approximately 15 to 40 mg/g of total protein. Most preferably the final concentration of L-carnitine is 25 mg/g of total protein. Many publications have shown-that damaged cardiac muscle functions better when supplemented with L-carnitine.

The nutritional composition also contains a carbohydrate source. The carbohydrate source preferably includes xylitol and a glucose-based carbohydrate. In a preferred embodiment the carbohydrate source includes maltodextrin and xylitol. The glucose substrate and xylitol are preferably present in a 1:1 ratio by weight. The carbohydrate source can also include ribose. In a preferred embodiment, the composition contains maltrodextrin, xylitol, and ribose in a preferred ratio of approximately 1:1:.066 by weight. In another embodiment, the composition contains maltrodextrin and xylitol preferably in a ratio of approximately 1:1 by weight The use of carbohydrates such as xylitol or ribose in nutritional support of individuals susceptible to and/or under treatment for cardiovascular disease is based upon the unique pathways for the metabolism of these compounds. Xylitol is a naturally occurring intermediate in the glucuronic acid-xylulose cycle, and may also be metabolized through the generation of the intermediate compound xylulose to form ribose. Accordingly, the administration or ingestion of the xylitol, xylulose, and/or ribose provides conversions of these intermediates to glucose. By providing a glucose-based carbohydrate source, i.e., maltodextrin, conversion of these compounds to glucose is minimized. The administration of a 1 to 1 ratio of glucose substrates with xylitol and ribose represents an effective means to maximize glucose production with minimal insulin elevation, while enhancing adenine nucleotide synthesis for this patient population.

The effect of ribose on cardiac function and ischemic events may be related to several specific functions of the compound. Administration of ribose to cardiac tissue following oxygen deprivation has been demonstrated to result in a 90% increase in the de novo synthesis of myocardial adenine nucleotides, as well as in the elevation of 5-phosphoribosyl-1-pyrophosphate (PRPP) specific pool in myocardial tissue. Continuous infusion of ribose has been demonstrated to result in a 13-fold increase in myocardial adenine nucleotide synthesis. Such elevations have further been demonstrated to reduce the occurrence of cell lesions in the myocardium.

It has been suggested that cellular depletion of compartmentalized ATP may be primarily responsible for the pathological effects of the ischemic event, through an imbalance between subcellular phosphocreatine and compartmentalized ATP. ATP may also serve as a modulator of myocardial cell function, responsible for potassium exchange and calcium:sodium exchange. These reactions require higher concentrations of ATP than those required for the PRPP pool alone. Demonstration of a marked effect of ribose administration on protection against isoproterenol-induced myocardial cell damage further supports the hypothesis for a role in cellular depletion of adenine nucleoides in the progression of cardiac necrosis.

The lipid component of the nutritional composition comprises long chain triglycerides and medium chain fatty acids. Preferably, the long chain triglycerides comprise "marine oils" and/or gamma-linolenic acid and sterodonic acid. The long chain triglycerides encompass trigylcerides containing fatty acids of 11 to 26 carbons in length. These fatty acids can be both saturated and unsaturated in nature. It has been shown that monounsaturated fatty acids are effective in lowering plasma cholesterol. Accordingly, preferably monounsaturated fatty acids are utilized as a component of these lipid substrates.

The medium chain fatty acids preferable in the present invention are those that are 6 to 10 carbons in length. These medium chain fatty acids are a superior energy source for the cardiac muscle cells. The fatty acids can be provided to patients as free fatty acids, mono-, di- or triglycerides. Medium chain fatty acids are chemically unique in that in the absence of cytoplasmic medium chain fatty acyl CoA synthetase they are able to pass through the inner mitochondrial membrane unhindered. Medium chain fatty acyl CoA synthetase does exist in the mitochondria and activates the fatty acids once they have crossed the inner membrane. These activated fatty acids are then rapidly metabolized.

In contrast, long chain fatty acids, i.e., those fatty acids having 11 to 26 carbons, due to their chemical nature cannot cross the inner mitochondrial membrane without being first activated by cytoplasmic long chain fatty acyl CoA synthetase, a rate limiting process. The long chain fatty acids must then undergo obligatory conversion to a carnitine transport form for entry into the mitochondria for metabolism.

Medium chain fatty acids combine their unique ability to cross the mitochondria membrane with the unique biochemical milieu of the cardiac cell. The cardiac muscle lacks cytoplasmic medium chain acyl CoA synthetase and the ability to activate medium chain fatty acids. Thus, medium chain fatty acids rapidly enter the mitochondria and supply energy in these cells directly. Long chain fatty acids cannot do this because of their necessary cytoplasmic activation and the slower carnitine transport in this organ.

The long chain triglycerides preferably comprise marine oils and/or gamma-linolenic acid (GLA) and/or sterodonic acid. The marine oils preferably include linolenic acid and large amounts of two other members of the omega three family: eicosapentaenoic acid (EPA) and docosahexaenoic acid (DHA). These fatty acids are incorporated into cell membranes and serum lipids and give rise to metabolites of the omega-three metabolic pathways. GLA is an omega-6 fatty acid and is a precursor to the 1-series prostaglandins.

Preferably the long chain triglycerides comprise from approximately 50% to about 25% of the lipid component and the medium chain fatty acids comprises from approximately 75% to about 50% of the lipid component. If GLA is utilized with marine oil, preferably approximately three times as much marine oil is used as GLA.

All cells utilize these fatty acids to form various prostaglandins and leukotrienes. When fatty acids are released from cell membranes, lipoxygenase and cyclooxygenase mediate further metabolic activity. Although EPA is a relatively poor substrate for lipoxygenase and cyclooxygenase, it appears to have a high binding affinity and thereby inhibits arachidonic acid conversion by these enzymes. An added benefit of the omega three fatty acid pathway lies in the physiological activity of their cellular products (See Table I - $PGI_2$=2-series prostacyclin; $PGI_3$=3-series prostacyclin; $TXA_2$=2-series thromboxane; and $TXA_3$=3-series thromboxane).

TABLE I

| Cell | Fatty Acid | Product | Physiological Actions |
|---|---|---|---|
| Endothelial | Arachidonic | $PGI_2$ | Lower platelet activity: vasodilation |
| | Eicosapentaenoic | $PGI_3$ | Lower platelet activity: vasodilation |
| Platelet | Arachidonic | $TXA_2$ | Platelet hyperactivity: vasoconstriction |
| | Eicosapentaenoic | $TXA_3$ | Lower platelet activity: vasoconstriction |

In most subjects who consume such diets, total serum cholesterol, LDL cholesterol, and triglycerides are significantly lowered, whereas HDL cholesterol concentrations are elevated. This pattern of change would be one thought to be less atherogenic and the thrombogenic.

Studies conducted with human platelets utilizing pure EPA and arachidonic acid support the role of the balance of EPA and arachidonic acid as the critical factor in controlling platelet activators and vessel constriction.

The electrolytes component of the present invention preferably includes sodium, potassium, chloride, calcium, magnesium, and phosphorus.

Preferably the protein source comprises approximately 15 to about 25% of the caloric source of the enteral nutritional composition. Most preferably the protein source comprises approximately 20% of the caloric source of the enteral nutritional composition. Preferably, the carbohydrate source comprises approximately 40% to about 75% of the caloric source of the enteral nutritional composition. Most preferably, the carbohydrate source comprises approximately 50% of the caloric source of the enteral nutritional composition. Preferably the lipid component comprises approximately 10% to about 40% of the caloric source of the enteral nutritional composition. Most preferably the lipid component comprises approximately 30% of the caloric source of the enteral nutritional composition.

By way of example, and not limitation, two preferred enteral cardiac formulations will no be set forth.

TABLE II

| CARDIAC FORMULATION | |
|---|---|
| Form: | Liquid |
| Concentration: | 2.0 kcal/ml |
| Protein Source: | Lactalbumin |
| | L-Carnitine |
| | Enhance BCAA |
| | Hi Arg: lys ratio |
| | Inc. Glycine |
| Gm/Liter | 100 |
| % Cal | 20 |
| Carbohydrate Source: | Maltodextrin |
| | Xylitol, |
| | Ribose |
| Ratio: | 1.0:1.0:.066 |
| Gm/Liter | 121,121,8 |
| % Cal | 50 |
| Fat Source: | Marine Oil (MO) |
| | GLA, MCT |
| Gm/Liter MCT&LCT | 57.7 |
| MO:GLA:MCT | 3:1:12 |
| % Cal | 30 |
| Electrolytes: | |
| Na/Liter | 500 mg |
| | 21.8 mEq |
| K/Liter | 1000 mg |
| | 35.4 mEq |
| Cl/Liter | 1000 mg |
| | 28.3 mEq |
| Ca/Liter | 1200 mg |
| P/Liter | 1000 mg |
| Mg/Liter | 600 mg |

TABLE III

| CARDIAC FORMULATION | |
|---|---|
| Form: | Liquid |
| Concentration: | 2.0 kcal/ml |
| Protein Source: | Lactalbumin |
| | L-Carnitine |
| | Enhance BCAA |
| | Hi Arg: lys ratio |
| | Inc. Glycine |
| Gm/Liter | 100 |
| % Cal | 20 |
| Carbohydrate Source: | Maltodextrin |
| | Xylitol |
| Ratio: | 1.0:1.0 |
| Gm/Liter | 125,125 |
| % Cal | 50 |
| Fat Source: | Marine Oil (MO) |
| | GLA, MCT |
| Gm/Liter MCT&LCT | 57.7 |
| MO:GLA:MCT | 3:1:12 |
| % Cal | 30 |
| Electrolytes: | |
| Na/Liter | 500 mg |
| | 21.8 mEq |
| K/Liter | 1000 mg |
| | 35.4 mEq |
| Cl/Liter | 1000 mg |
| | 28.3 mEq |
| Ca/Liter | 1200 mg |
| P/Liter | 1000 mg |
| Mg/Liter | 600 mg |

The parenteral regimen for the composition for providing nutritional support or therapy for individuals at risk or under therapy for vascular, cardiovascular, or thrombotic disease is preferably modular. However, the parenteral regimen can be premixed before use. The parenteral regimen solution for injection contains: a lipid emulsion; a carbohydrate solution; carnitine; branched-chain amino acids; and amino acids.

Preferably, the lipid emulsion for injection includes approximately 5 to about 20% of a triacylglycerol oil containing approximately 5 to about 80% eicosapentaenoic acid (EPA) and/or approximately 5 to about 80% gamma-linolenic acid (GLA) and approximately 3 to about 25% sterodonic acid (6, 9, 12, 15-octadecatetraenoic acid), with approximately 0.4 to about 1.6% egg or soy bean phospholipid and approximately 2.25% of glycerol or other physiologically acceptable tonicity agent, adjusted to physiological pH with sodium hydroxide. Water or water and medium chain triglycerides comprise the remainder of the lipid emulsion. If medium chain triglycerides are used they comprise no more than 30% (w/v) of the lipid emulsion.

The carbohydrate injection solution preferably contains glucose and xylitol in an approximately 1:1 ratio by weight. The solution can contain in an embodiment approximately 3.3% (w/v) ribose.

To the branched-chain amino acid injection solution can be added any other amino acid capable of necessary to meet nutritional requirements. The branched-chain amino acid injection solution contains Isoleucine, Leucine, and Valine, preferably in a 1:1:1 molar ratio.

The solution for injection of amino acids can contain essential, non-essential, and conditionally essential amino acids. Preferably the solution includes: L-Arginine; L-Leucine; L-Isoleucine; L-Lysine; L-Valine; L-Phenylalanine: L-Histidine: L-Threonine; L-Methionine; L-Tryptophan; L-Alanine; L-Proline; L-Serine; L-Tyrosine; and amino acetic acid. However, the solution can contain less than all these amino acids, or other nutrients such as, for example, taurine and cysteine. An example of such an amino acid solution and the relevant proportions of each amino acids is TRAVASOL® marketed by Travenol Laboratories, Deerfield, Ill.

By way of example, and not limitation, contemplated examples will now by given.

EXAMPLE ONE

This contemplated example demonstrates the use of the parenteral cardiac formulation in providing nutrition and therapy to a patient suffering cardiovascular disease.

A middle-aged male patient is admitted to intensive care following an acute myocardial infarction. Among the therapies administered would be the parenteral cardiac formulation as part of a continuous intravenous infusion. The parenteral cardiac formula includes: a lipid emulsion injection; a carbohydrate injectable solution; injectable carnitine; injectable branched-chain amino acid solution; and an injectable amino acid solution. The lipid emulsion for injection includes 10% of a triacylglycerol oil containing 15% eicosapentaenoic acid (EPA) and 5% gamma-linolenic acid (GLA) and 5% sterodonic acid with 1.2% soybean phospholipid and approximately 2.25% of glycerol and water. The carbohydrate injection solution contains glucose and xylitol in am approximately 1:1 ratio by weight. The branched-chain amino acid injection solution contains Isoleucine, Leucine, and Valine, in a 1:1:1 molar ratio. The amino acid solution was TRAVASOL ®. The key critical features of this patient's clinical profile include:
cardiac ischemic with hyperactive platelets that can be easily triggered to aggregate, leading to a life-threatening secondary event involving thrombus formation and vasoconstriction of the coronary artery at the site of activation, increased vascular tone and a predisposition to vascular spasm.

As a result of this cardiac parenteral formulation, the patient's cardiac muscle tissue would have available energy and protein substrates and their platelets would be far less reactive within hours of the onset of I.V. administration. Furthermore, the balance of the 2-series prostacyclins and 3-series prostacyclin/2-series thromboxane ratio would begin to shift in a favorable direction, leading to a reduced risk of vascular spasm.

EXAMPLE TWO

This same patient, as described in example one, recovers and is sent home to follow a strict regimen. He has advanced atherosclerosis, the sequellae of which include hypertension, elevated serum triglycerides and LDL, VLDL, and total cholesterol concentrations, low serum HDL cholesterol concentration, and a very high risk of stroke, myocardial infarction, or other thrombotic events.

Doctors focus on dietary control of this disease process, to supplement prescribed medications. The cardiac enteral diet set forth in Table II as a nutritional supplement provides necessary cardiac muscle nutrition as well as the therapeutic effects of EPA/DHA. Consumed on a daily basis, this diet would:
1. provide specialized cardiac muscle protein;
2. provide carbohydrate and calorie nutrition;
3. lower serum triglyceride and LDL, VLDL, and total cholesterol concentrations;
4. markedly reduce platelet reactivity, leading to reduced incidence of thromboxane and serotonin release by platelets (vasoactive stimulators and platelet activators) as well as platelet derived growth factor release (a known atherogenic factor);
5. lower systolic blood pressure, another factor associated with atherogenesis.

EXAMPLE THREE

In this contemplated example, a patient with cardiovasulcar disease requires a vascular graft. The highest risk for graft-associated thrombosis occurs within the first week following graft placement. Since this is a platelet/white blood cell-mediated event, placing this patient on a combined parenteral (set forth in Example One) and enteral (Table II) cardiac formulation for 7-10 days, while in recovery, will markedly dampen both platelet and white blood cell reactivity as well as provide essential nutritional support.

Following release from hospital, this patient could continue with the daily consumption of the parenteral and/or enteral formulation to maintain a low thrombogenic potential.

EXAMPLE FOUR

In this contemplated example, an elderly patient following hip surgery is committed to several weeks of bed rest. There is a recognized marked thrombotic tendency following this procedure, partly due to the surgery itself, and partly to the prolonged vascular stasis resulting from the elimination of physical activity.

A regimen of combined enteral (Table II) and parenteral (set forth in Example One) cardiac formulation for a week following surgery, and a continuation of the enteral formulation during the remainder of the recovery period, will not only dampen the thrombotic tendency, but also will provide essential nutrients to support the healing process in this elderly patient.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:
1. A method for providing cardiac therapy to an individual in need of same through a parenteral regimen comprising:
   a. a therapeutically effective amount of a protein source which includes a high biological value protein, amino acids including branched-chain amino acids and L-carnitine;
   b. a therapeutically effective amount of a polysaccharide source supplemented with ribose and/or xylitol; and
   c. a therapeutically effective amount of a lipid emulsion consistently essentially of a natural oil containing unsaturated fatty acids of 11 to 26 carbons in length, and an emulsifier.
2. The method of claim 1, wherein said natural oil comprises 5 to 20% of the lipid emulsion.
3. The method of claim 1, wherein the amino acids include: L-Arginine; L-Leucine; L-Isoleucine; L-Lysine; L-Valine; L-Phenylalanine; L-Histidine; L-Threonine; L-methionine; L-Tryptophan; L-Alanine; L-Proline; L-Serine; L-Tyrosine; amino acetic acid; isoleucine; leucine; and valine.
4. The method of claim 1, wherein said medium chain fatty acids comprise 50 to about 75% of the total lipid content.
5. A method of providing cardiac therapy to an individual in need of same utilizing an enteral regimen comprising:
   a. a therapeutically effective amount of a protein source which includes a high biological value protein, amino acids including branched-chain amino acids and L-carnitine;
   b. a therapeutically effective amount of a polysaccharide source supplemented with ribose and/or xylitol; and
   c. a therapeutically effective amount of a lipid emulsion consistently essentially of a natural oil containing unsaturated fatty acids of 11 to 26 carbons in length, and an emulsifier.

6. The method of claim 5, wherein said natural oil comprises 5 to 20% of the lipid emulsion.

7. The method of claim 5 wherein the amino acids include: L-arginine; L-leucine; L-isoleucine; L-lysine; valine; L-phenylalanine; L-histidine; L-threonine; L-methionine; L-tryptophan; L-alanine; L-proline; L-serine; L-tyrosine; amino acetic acid; isoleucine; leucine; and valine.

8. The method of claim 5, wherein said medium chain fatty acids comprise 50 to about 75% of the total lipid content.

9. A method for providing therapy to an individual at risk or under treatment for vascular, cardiovascular, or thrombotic diseases comprising the steps of:
   a. administering a therapeutically effective amount of a protein source which includes a high biological value protein, amino acids including branched-chain amino acids and L-carnitine;
   b. administering a therapeutically effective amount of a polysaccharide source supplemented with ribose and/or xylitol; and
   c. administering a therapeutically effective amount of a lipid emulsion consistently essentially of a natural oil containing unsaturated fatty acids of 11 to 26 carbons in length, and an emulsifier.

10. The method of claim 9, wherein said natural oil comprises 5 to 20% of the lipid emulsion.

11. The method of claim 9, wherein the amino acids include: L-arginine; L-leucine; L-isoleucine; L-lysine; L-valine; L-phenylalanine; L-histidine; L-theronine; L-methionine; L-tryptophan; L-alanine; L-proline; L-serine; L-tyrosine; amino acetic acid; isoleucine; leucine; and valine.

12. The method of claim 5, wherein said medium chain fatty acids comprise 50 to about 75% of the total lipid content.

13. The method of claim 9 including the step of administering the protein source, polysaccharide source, and lipid emulsion parenterally.

14. The method of claim 9 including the step of administering the protein source, polysaccharide source, and lipid emulsion enterally.

* * * * *